US006586199B2

(12) United States Patent
Ouyang et al.

(10) Patent No.: US 6,586,199 B2
(45) Date of Patent: *Jul. 1, 2003

(54) STABILIZED TETRAZOLIUM REAGENT COMPOSITIONS AND METHODS FOR USING THE SAME

(75) Inventors: Tianmei Ouyang, Fremont, CA (US); Paing Huang, San Francisco, CA (US)

(73) Assignee: LifeScan, Inc., Milpitas, CA (US)

(*) Notice: Subject to any disclaimer, the term of this patent is extended or adjusted under 35 U.S.C. 154(b) by 8 days.

This patent is subject to a terminal disclaimer.

(21) Appl. No.: 09/988,812

(22) Filed: Nov. 20, 2001

(65) Prior Publication Data

US 2003/0096332 A1 May 22, 2003

(51) Int. Cl.[7] .............................. C12Q 1/26; C12Q 1/32; C12Q 1/54
(52) U.S. Cl. .............................. 435/26; 435/25; 435/14; 435/4; 435/975
(58) Field of Search .............................. 435/26, 25, 14, 435/4, 975

(56) References Cited

U.S. PATENT DOCUMENTS 5,902,731 A * 5/1999 Ouyang et al. ............... 435/26

6,200,773 B1 * 3/2001 Ouyang et al. ............... 435/26

FOREIGN PATENT DOCUMENTS

| EP | 0908453 A1 | 4/1999 |
| WO | WO 94/01544 | 1/1994 |
| WO | WO 94/01578 | 1/1994 |

* cited by examiner

*Primary Examiner*—Louise N. Leary
(74) *Attorney, Agent, or Firm*—Carol M. LaSalle; Brett E. Field; Bozicevic, Field & Francis, LLP

(57) ABSTRACT

Stabilized tetrazolium dye reagent compositions and methods for their use in the measurement of an analyte in a sample are provided. The subject reagent compositions include a tetrazolium dye component, e.g., a water soluble tetrazolium salt, and an effective amount of a nitrite stabilizing agent, e.g., a nitrite salt. In many embodiments, the subject reagent compositions include additional members of an analyte oxidizing signal producing system, such as: an analyte oxidizing enzyme, e.g., an analyte dehydrogenase or an analyte oxidase; an electron transfer agent; and an enzyme cofactor. Also provided are test strips that include the subject reagent compositions, as well as systems and kits incorporating the subject test strips. The subject reagent compositions, test strips, systems and kits find use in the detection of a wide variety of analytes in a sample, such as a physiological sample, e.g., blood or a fraction thereof, or ISF (interstitial fluid).

32 Claims, 4 Drawing Sheets

STABILIZED TETRAZOLIUM REAGENT COMPOSITIONS AND METHODS FOR USING THE SAME

FIELD OF THE INVENTION

The field of this invention is analyte measurement

BACKGROUND OF THE INVENTION

Analyte measurement in physiological fluids, e.g., blood or blood derived products, is of ever increasing importance to today's society. Analyte detection assays find use in a variety of applications, including clinical laboratory testing, home testing, etc., where the results of such testing play a prominent role in diagnosis and management in a variety of disease conditions. Analytes of interest include alcohol, formaldehyde, glucose, glutamic acid, glycerol, beta-hydroxybutyrate, L-lactate, leucine, malic acid, pyruvic acid, steroids, etc. In response to this growing importance of analyte measurement, a variety of analyte measurement protocols and devices for both clinical and home use have been developed.

Many of the protocols and devices that have been developed to date employ a signal producing system to identify the presence of the analyte of interest in a physiological sample, such as blood.

While a variety of such signal producing systems have been developed to date for use in the measurement of a wide variety of different analytes, there continues to be a need for the further development of such systems.

Relevant Literature

Patent documents of interest include: U.S. Pat. No. 6,200,773; U.S. Pat. No. 5,902,731; EP 0 908 453 A1; WO 94/01578 and WO 94/01544.

SUMMARY OF THE INVENTION

Stabilized tetrazolium dye reagent compositions that include a tetrazolium dye reagent, e.g., a water soluble tetrazolium salt, and a nitrite tetrazolium dye stabilizing reagent, e.g., a nitrite salt, are provided. In many embodiments, the reagent compositions include members of analyte oxidizing signal producing system of which the tetrazolium dye is a member, which system includes one or more of the following additional components: an analyte oxidizing enzyme, e.g., an analyte dehydrogenase or an analyte oxidase; an electron transfer agent; and an enzyme cofactor. Also provided are test strips that include the subject reagent compositions, as well as systems and kits incorporating the subject test strips. The subject reagent compositions, test strips, systems and kits find use in the measurement of a wide variety of analytes in a sample, such as a physiological sample, e.g., blood or a fraction thereof, or ISF (interstitial fluid).

DESCRIPTION OF THE SPECIFIC EMBODIMENTS

Figure 1:
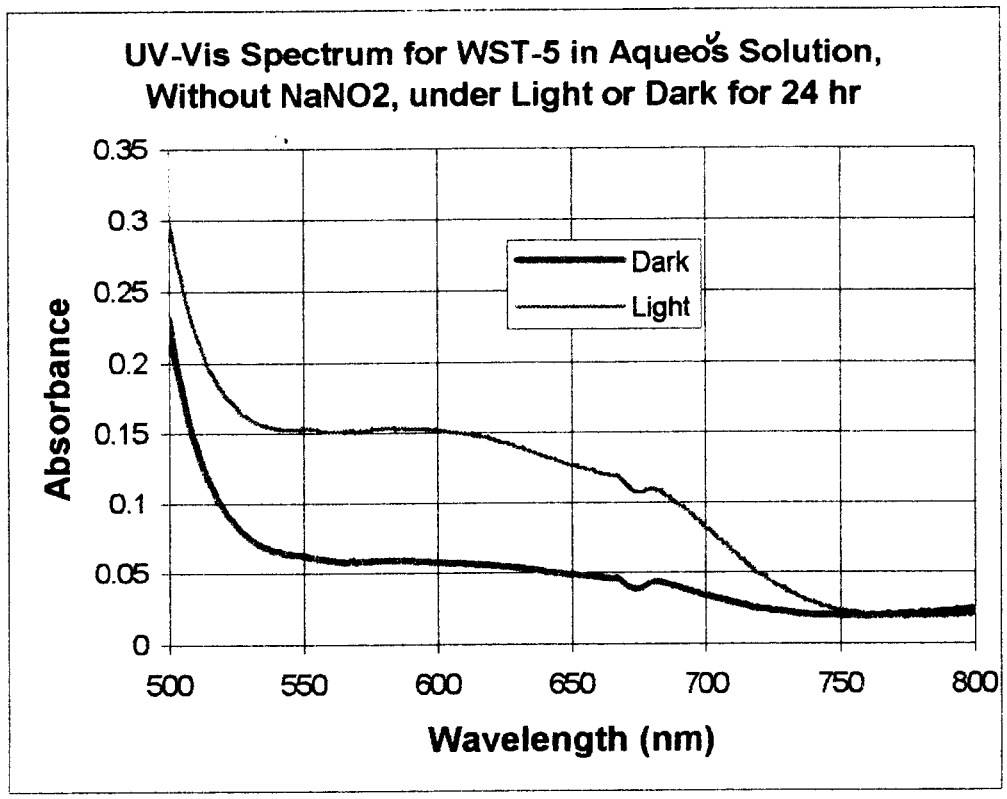
FIG. 1 provides the UV-Vis spectrum for WST-5 in aqueous solution, without $NaNO_2$, under light or dark for 24 hr.

Stabilized tetrazolium dye reagent compositions and methods for their use in the measurement of an analyte in a sample are provided. The subject reagent compositions include a tetrazolium dye component, e.g., a water soluble tetrazolium salt, and an effective amount of a nitrite stabilizing agent, e.g., a nitrite salt. In many embodiments, the subject reagent compositions include additional members of an analyte oxidizing signal producing system, such as: an analyte oxidizing enzyme, e.g., an analyte dehydrogenase or an analyte oxidase; an electron transfer agent; and an enzyme cofactor. Also provided are test strips that include the subject reagent compositions, as well as systems and kits incorporating the subject test strips. The subject reagent compositions, test strips, systems and kits find use in the detection of a wide variety of analytes in a sample, such as a physiological sample, e.g., blood or a fraction thereof, or ISF (interstitial fluid).

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the components that are described in the publications which might be used in connection with the presently described invention.

As summarized above, the subject invention provides stabilized tetrazolium dye compositions and methods for their use, as well as reagent test strips, systems and kits. In further describing the invention, each of these inventive features are discussed in greater detail below.

Reagent Compositions

As summarized above, the subject invention provides stabilized tetrazolium dye reagent compositions, which compositions find use in detecting a wide variety of analytes in a sample. The subject tetrazolium dye reagent compositions of the present invention are characterized by at least including a tetrazolium dye reagent and an effective amount of a nitrite stabilizing reagent.

The tetrazolium dye reagent is a tetrazolium compound (dye precursor) that, upon acceptance of a transferred hydride, forms a colored formazan product. In many embodiments, the tetrazolium dye reagent is a water soluble tetrazolium salt that is capable of accepting a hydride to produce a water soluble, colored formazan product. Water soluble tetrazolium salts of interest include those described in EP 0 908 453, the disclosure of which is herein incorporated by reference. One class of water soluble tetrazolium salts of interest include those described by formula 2 on page 2, lines 35 to 48 of EP 0 908 453. Another class of water soluble tetrazolium salts of interest include those described by formula 1 on page 3, lines 10–25 of EP 0 908 453.

Specific water soluble tetrazolium compounds or salts that are of particular interest include, but are not limited to: 2-(2'benzothiazolyl)-5-styryl-3-(4'-phthalhydrazidyl) tetrazolium (BSPT), 2-benzothiazolyl-(2)-3,5-diphenyl tetrazolium (BTDP), 2,3-di(4-nitrophenyl)tetrazolium (DNP), 2,5-diphenyl-3-(4-styrylphenyl)tetrazolium (DPSP), distyryl nitroblue tetrazolium (DS-NBT), 3,3'-[3,3'-dimethoxy-(1,1'-biphenyl)-4,4'-diyl]-bis[2-(4-nitrophenyl)-5-ph enyl(-2H tetrazolium (NBT), 3-(4,5-dimethyl-2-thiazolyl)-2,5-diphenyl-2H tetrazolium (MTT), 2-phenyl-3-(4-carboxyphenyl)-5-methyl tetrazolium (PCPM), tetrazolium blue (TB), thiocarbamyl nitroblue tetrazolium (TCNBT), tetranitroblue tetrazolium (TNBT), tetrazolium violet, (TV), 2-benzothiazothiazolyl-3-(4-carboxy-2-methoxyphenyl)-5-[4-(2-sulfoethylcar bamoyl)phenyl]-2H-tetrazolium (WST-4), and 2,2'-dibenzothiazolyl-5,5'-bis[4-di(2-sulfoethyl)carbamoylphenyl]-3,3'-(3,3'-dimethoxy-4, 4'-biphenylene)ditetrazolium, disodium salt (WST-5). In certain embodiments, the dye compounds is selected from the group of: 2,2'-dibenzothiazolyl-5,5'-bis[4-di(2-sulfoethyl)carbamoylphenyl]-3,3'-(3,3'-dimethoxy-4,4'-biphenylene)ditetrazolium, disodium salt (WST-5); 2-benzothiazolyl-3-(4-carboxy-2-methoxyphenyl)-5-[4-(2-sulfoethylcarbamoyl)phenyl]-2H-tetrazolium (WST-4) and the like. WST-5 is preferred in many embodiments because it readily dissolves in an aqueous medium, which is most compatible with biological samples. Furthermore, the resulting formazan compound exhibits strong spectral absorption at the purple-blue region, thus reducing the need for correcting the background signal from hemoglobin. While the amount of the tetrazolium dye reagent may vary depending on the nature of the reagent composition, e.g., whether it is in dry or wet form, the concentration of the dye reagent in many embodiments ranges from about 1.5 mM to about 50 mM, usually from about 3 mM to about 40 mM and more usually from about 3.5 mM to about 28 mM.

In addition to the tetrazolium dye compound described above, the subject reagent compositions also include an effective amount of a nitrite stabilizing agent. By effective amount is meant an amount sufficient to stabilize the tetrazolium compound so that it is not adversely compromised or affected, e.g., altered, by exposure to light. In other words, the amount of nitrite stabilizing agent employed is one that is sufficient to provide for a stabilized tetrazolium compound that provides substantially equal signal characteristics regardless of whether it is exposed to light or dark prior to characterization. A tetrazolium dye compound present in a liquid reagent composition is considered to be stabilized for purposes of this invention if any difference in its signal generating properties following exposure to light does not exceed about 2 fold, usually about 2.5 fold as compared to the signal properties observed when it is not exposed to light, as determined using the evaluation protocol reported in Example 1, below. A tetrazolium dye compound present in a dry reagent composition is considered to be stabilized for purposes of this invention if any difference in its signal generating properties following exposure to light does not exceed about 2 fold, usually about 2.3 fold as compared to the signal properties observed when it is not exposed to light, as determined using the evaluation protocol reported in Example 2, below. The ratio of nitrite stabilizing component to tetrazolium dye in the composition typically ranges from about 2 to about 500, usually from about 7 to about 200. As such, in many embodiments, the concentration of the nitrite stabilizing reagent in the composition ranges from about 0.1 M to about 0.8M usually from about 0.2 M to about 0.6 M. While any suitable nitrite stabilizing agent may be employed, of particular interest are nitrite salts, such as sodium nitrite, potassium nitrite, and their derivatives, where sodium nitrite is of particular interest in many embodiments of the invention. The presence of the nitrite stabilizing agent stabilizes the tetrazolium dye with respect to light exposure of at least about 3 hours, often at least about 5 hours and sometimes at least about 10, 15, 20, 24, 48, 72 hours or more.

As mentioned above, the subject reagent compositions typically further include additional members of an analyte oxidizing signal producing system. By signal producing system is meant a collection of two or more compounds or molecules which are capable of acting in concert, when combined, to produce a detectable signal that is indicative of the presence of, and often amount of, a particular analyte in a given sample. The term signal producing system is used broadly to encompass both a mixture of all of the reagent constituents of the signal producing system as well as a system in which one or more of the reagent constituents are separated from the remainder of the reagent constituents, e.g., as is present in a kit.

As mentioned above, the signal producing system of the subject compositions is an analyte oxidizing signal producing system. The analyte oxidizing agent is generally an enzyme that is capable of removing a hydride from the analyte of interest to produce an oxidized form of the analyte. Analyte oxidizing enzymes of interest include analyte oxidases and analyte dehydrogenases. Analyte oxidases of interest include, but are not limited to: glucose oxidase (where the analyte is glucose); cholesterol oxidase (where the analyte is cholesterol); alcohol oxidase (where the analyte is alcohol); bilirubin oxidase (where the analyte is bilirubin); choline oxidase (where the analyte is choline); formaldehyde dehydrogenase (where the analyte is formaldehyde); glutamate oxidase (where the analyte is L-glutamic acid); glycerol oxidase (where the analyte is glycerol); galactose oxidase (where the analyte is galactose); L-ascorbate oxidase (where the analyte is ascorbic acid); lactate oxidase (where the analyte is lactic acid); leucine oxidase (where the analyte is leucine); malate oxidase (where the analyte is malic acid); pyruvate oxidase (where the analyte is pyruvic acid); urate oxidase (where the analyte is uric acid); and the like.

Analyte dehydrogenases of interest include, but are not limited to: alcohol dehydrogenase for alcohol; formaldehyde dehydrogenase for formaldehyde; glucose dehydrogenase for glucose; glucose-6-phosphate dehydrogenase for glucose-6-phosphate; glutamate dehydrogenase for glutamic acid; glycerol dehydrogenase for glycerol; beta-hydroxybutyrate dehydrogenase for beta-hydroxybutyrate; hydroxysteroid dehydrogenase for steroid; L-lactate dehydrogenase for L-lactate; leucine dehydrogenase for leucine; malate dehydrogenase for malic acid, and pyruvate dehydrogenase for pyruvic acid.

In many embodiments, the subject signal producing systems also include an enzyme cofactor that is capable of interacting with the oxidizing agent in a manner such that the analyte of interest is oxidized by the oxidizing agent, which agent concomitantly reduces the enzyme cofactor. Enzyme cofactors of interest include, but are not limited to: i.e., beta-nicotinamide adenine dinucleotide (beta-AND); beta-nicotinamide adenine dinucleotide phosphate (beta-NADP); thionicotinamide adenine dinucleotide; thionicotinamide adenine dinucleotide phosphate; nicotinamide 1,N6-ethenoadenine dinucleotide; nicotinamide 1,N6-ethenoadenine dinucleotide phosphate; and pyrroloquinoline quinone (PQQ); and flavin copmpounds, such as FAD and FMN. Enzyme cofactors of particular interest that may be included in the subject signal producing systems include: NADH or AND(P)H and PQQH2.

In addition to the analyte oxidizing agent, the subject signal producing systems typically include an electron transfer agent. By electron transfer agent is meant a compound or molecule that can transfer an electron, in the form of a hydride ion, from a reduced enzyme cofactor to the water soluble tetrazolium product. Electron transfer agents of interest include both low and high molecular weight electron transfer agents. In this specification, low molecular weight means a molecular weight that does not exceed about 2000 daltons, usually about 1000 daltons and in many embodiments about 500 daltons. High molecular weight means a molecular weight of at least about 5000 daltons and in many embodiments 10,000 or 20,000 daltons or higher. The molecular weight of the high molecular weight electron transfer agent often will not exceed about 100,000 daltons. In many embodiments, the low molecular weight electron transfer agent is a non-proteinaceous compound while the high molecular weight electron transfer agent is a proteinaceous compound. By proteinaceous is meant a polypeptide or polymeric mimetic thereof.

A variety of low molecular weight non-proteinaceous electron transfer agents are of interest. These agents include: flavins such as riboflavin (RBF), alloxazine (ALL) and lumichrome (LC); phenazines such as phenazine, phenazine methosulfate (PMS), phenazine ethosulfate, methoxyphenazine methosulfate and safranine; methyl-1, 4-naphthol (menadione), phenothiazines such as PT and its radical cation, PT+, thionin (TH), azure A (AA), azure B (AB), azure C (AC), methylene blue (MB), methylene green (MG) and toluidine blue O (TOL); phenoxazines such as phenoxazine (POA), basic blue 3 (BB3), and brilliant cresyl blue ALD (BCBA), benzo-α-phenazoxonium chloride (Medola's blue); Indophenols such as 2,6-dichlorophenol indophenol (DCIP); and Indamines such as Bindschedler's green and phenylene blue; and the like. Of particular interest in many embodiments are phenazine compounds, e.g. PMS, phenazine ethosulfate, methoxyphenazine methosulfate and safranine, where PMS is the low molecular weight, non-proteinaceous electron transfer agent in many embodiments.

In many embodiments, the high molecular weight proteinaceous electron transfer agent is an enzyme that is capable of oxidizing a reduced cofactor, e.g. NAD(P)H, and concomitantly reducing the tetrazololium salt of the signal producing system. In many embodiments, this electron transfer enzyme is a diaphorase, such as lipoic dehydrogenase, ferredoxin-NADP reductase, lipoamide dehydrogenase, NADPH dehydrogenase, etc. A variety of diaphorases are available and may be employed, where representative commercially available diaphorases that may be present in the subject signal producing systems include bacillus diaphorase, clostridium diaphorase, vibrio diaphorase, porcine diaphorase, and the like.

As indicated above, the subject compositions are present as either wet or dry compositions. By wet composition is meant a fluid composition, typically an aqueous composition. Such compositions find use in various assay configurations, such as cuvette configurations, which are well known in the art. By dry compositions is meant a composition that is not fluid, i.e., in dry form, such as a composition that is substantially free of uncombined water. Such compositions are typically found in reagent test strips, as described in greater detail below.

Reagent Test Strips

Of particular interest in many embodiments of the subject invention are reagent test strips that include the above described dry reagent compositions and are intended for use in measuring the presence or concentration of an analyte in a sample. In particular, the invention provides dry strips for assaying for a particular analyte in whole blood, e.g., beta-hydroxybutyrate, glucose, etc. In the broadest sense, the reagent test strip includes a solid support and a dry reagent composition present thereon, where the dry reagent composition is made up of all of the reagent compounds necessary to produce a detectable signal in the presence of the analyte of interest. In most embodiments of the subject invention, the dry reagent composition present on the subject test strip is one that includes the following members: an analyte oxidizing enzyme, an enzyme cofactor, an electron transfer agent, a water soluble tetrazolium salt, and a nitrite stabilizing reagent, where each of these constituent members are described in greater detail above.

In many embodiments, the subject test strips include a membrane test pad that is affixed to a solid support. The support may be a plastic—e.g., polystyrene, nylon, or polyester—or metallic sheet or any other suitable material known in the art. Associated with the test pad, e.g., coated onto the test pad, incorporated into the test pad, etc., is the reagent composition. The strip may also be configured in more complex arrangements, e.g., where the test pad is present between the support and a surface layer, where one or more reagents employed in sample processing may be present on the surface layer. In addition, flow paths or channels may be present on the test strip, as is known in the art. Of interest in many embodiments are the test strip configurations disclosed in U.S. Pat. No. 5,902,731, the disclosure of which is herein incorporated by reference.

In the subject test strips, the dry reagent composition is associated with, e.g., present on or in, a carrier material or substrate. The substrate may be bibulous or non-bibulous. By bibulous is meant a material that exhibits preferential retention of one or more components as would occur, for example, in materials capable of absorbing or "imbibing" one or more components, as occurs in chromatographic separations. Examples of bibulous materials include, but are not limited to: nylon, untreated forms of paper, nitrocellulose and the like which result in chromatographic separation of components contained in liquids which are passed therethrough.

Alternatively, the substrate may be non-bibulous. Non-bibulous substrates include inert porous matrices which provide a support for the various members of the signal producing system, described infra, and may have a positive charge. These matrices are generally configured to provide a location for application of a physiological sample, e.g., blood, and detection of the chromogenic product produced by the dye of the signal producing system. As such, the matrix is typically one that is permissive of aqueous fluid flow through it and provides sufficient void space for the chemical reactions of the signal producing system to take place. A number of different porous matrices have been developed for use in various analyte measurement assays, which matrices may differ in terms of materials, pore sizes, dimensions and the like, where representative matrices include those described in U.S. Pat. Nos: 55,932,431; 5,874,099; 5,871,767; 5,869,077; 5,866,322; 5,834,001; 5,800,829; 5,800,828; 5,798,113; 5,670,381; 5,663,054; 5,459,080; 5,459,078; 5,441,894 and 5,212,061; the disclosures of which are herein incorporated by reference. The dimensions and porosity of the test strip may vary greatly, where the matrix may or may not have a porosity gradient, e.g., with larger pores near or at the sample application region and smaller pores at the detection region. In many embodiments, the matrix is configured as a membrane test pad and is affixed to a solid support, where the support may be a plastic (e.g., polystyrene, nylon or polyester) or metallic sheet or any other suitable material known in the art. Of interest in many embodiments are the test strip configurations disclosed in U.S. Pat. Nos. 5,972,294; 5,968,836; 5,968,760; 5,902,731; 5,846,486; 5,843,692; 5,843,691; 5,789,255; 5,780,304; 5,753,452; 5,753,429; 5,736,103; 5,719,034; 5,714,123; 383,550; 381,591; 5,620,863; 5,605,837; 5,563,042; 5,526,120; 5,515,170; 367,109; 5,453,360; 5,426,032; 5,418,142; 5,306,623; 5,304,468; 5,179,005; 5,059,394; 5,049,487; 4,935,346; 4,900,666 and 4,734,360, the disclosures of which are herein incorporated by reference.

Examples of suitable representative test strip configurations are provided in U.S. Pat. Nos. 6,200,733 and 5,902,731, the disclosures of which are herein incorporated by reference.

The subject test strips may be fabricated employing any convenient protocol. One convenient protocol is to contact at least the test pad portion of the strip with an aqueous composition that includes all of the members of the reagent composition that are to be associated with the test pad in the final reagent test strip. Conveniently, the test pad may be immersed in the aqueous composition, maintained therein for a sufficient period of time and then dried, whereby the test pad of the reagent test strip which has associated therewith the reagent composition is produced. As stated above, the aqueous composition will include the various members of the reagent composition to be associated with the test pad of the reagent test strip, where the various members are present in amounts sufficient to provide for the desired amounts in the reagent composition that is produced on the test pad. As such, where the electron transfer agent is non-proteinaceous, the concentration of electron transfer agent present in this aqueous composition typically ranges from about 10 to 50,000, usually from about 50 to 10,000 and more usually from about 100 to 5,000 $\mu$M. In other embodiment where the electron transfer agent is proteinaceous, the concentration of the electron transfer agent present in the aqueous composition typically ranges from about 10 to 10,000, usually from about 50 to 5,000 and more usually from about 100 to 3,000 U/ml. The concentration of tetrazolium dye, e.g., tetrazolium salt, present in the aqueous composition ranges from about 3 mM to 36 mM, usually from about 6 mM to 24 mM. When present, the enzyme cofactor ranges in concentration from about 1.5 mM to 28 mM, usually from about 3.5 mM to 14 mM. Similarly, the analyte oxidizing agent enzyme ranges in concentration from about 100 U to 5000 U, and usually from about 200 U to 3000 U when present. The amount of nitrite stabilizing agent, e.g., nitrite salt such as sodium nitrite, typically ranges from about 0.1 M to about 0.8M, usually from about 0.2 M to about 0.6 M. See the experimental section, infra, for a more detailed description of a representative method for preparing the subject reagent test strips.

Methods of Analyte Measurement

The above described signal producing systems, reagent compositions and test strips find use in methods of detecting the presence of, and often the amount of, i.e., the concentration of, an analyte in a sample. A variety of different analytes may be detected using the subject methods, where representative analytes include those described above, e.g., alcohol, formaldehyde, glucose, glutamic acid, glycerol, beta-hydroxybutyrate, L-lactate, leucine, malic acid, pyruvic acid, steroids, etc. While in principle, the subject methods may be used to determine the presence, and often concentration, of an analyte in a variety of different physiological samples, such as urine, tears, saliva, and the like, they are particularly suited for use in determining the concentration of an analyte in blood or blood fractions, e.g., blood derived samples, and more particularly in whole blood, ISF (interstitial fluid).

In the subject methods, the sample and the signal producing system are combined into a reaction mixture, the reaction is allowed to proceed for a sufficient period to time to generate a signal indicative of the presence of (and often amount of) analyte in the sample, and the resultant signal is detected and related to the presence of (and often amount of) analyte in the sample. The above steps may take place in a suitable volume containment means, e.g., cuvette, where the reagent composition is a fluid composition. In many embodiments, the above steps take place on a reagent test strip as described supra.

In certain embodiments, a feature of the subject methods is that the detectable signal is made up of a non-washable spot that forms on the surface of the substrate of the strip. The non-washable spot is made up of water soluble formazan product which is tightly bound to the substrate surface such that it cannot be readily removed from the surface under standard washing conditions. By standard washing conditions is meant the conditions experienced by substrate surface in analyte detection assays where unbound component has to be removed from the surface. An example of standard washing conditions are those employed by those of skill in the art in array based nucleic acid hybridization assays, where non-hybridized nucleic acids are removed from the surface of an array following a hybridization step. Such conditions are well known to those of skill in the art. As such, a feature of the subject methods is the production of a non-washable spot on the surface of the positively charged substrate, where the non-washable spot is made up of the water soluble formazan product.

In practicing many embodiments of the subject methods, the first step is to apply a quantity of the physiological sample to the test strip, where the test strip is described supra. The amount of physiological sample, e.g., blood, that is applied to the test strip may vary, but generally ranges from about 2 $\mu$L to 40 $\mu$L, usually from about 5 $\mu$L to 20 $\mu$L. Because of the nature of the subject test strip, the blood sample size that is applied to the test strip may be relatively small, ranging in size from about 2 $\mu$L to 40 $\mu$L, usually from about 5 μL to 20 μL. Where blood is the physiological sample, blood samples of a variety of different hematocrits may be assayed with the subject methods, where the hematocrit may range from about 20% to 65%, usually from about 25% to 60%.

Following application of the sample to the test strip, the sample is allowed to react with the members of the signal producing system to produce a detectable product, i.e., the non-washable spot, that is present in an amount proportional to the initial amount of the analyte of interest present in the sample. The amount of detectable product, i.e., signal produced by the signal producing system in the form of the non-washable spot, is then determined and related to the amount of analyte in the initial sample. In certain embodiments, automated instruments that perform the above mentioned detection and relation steps are employed. The above described reaction, detection and relating steps, as well as instruments for performing the same, are further described in U.S. Pat. Nos. 4,734,360; 4,900,666; 4,935,346; 5,059,394; 5,304,468; 5,306,623; 5,418,142; 5,426,032; 5,515,170; 5,526,120; 5,563,042; 5,620,863; 5,753,429; 5,573,452; 5,780,304; 5,789,255; 5,843,691; 5,846,486; 5,902,731; 5,968,836 and 5,972,294; the disclosures of which are herein incorporated by reference. In the relation step, the derived analyte concentration takes into account the constant contribution of competing reactions to the observed signal, e.g., by calibrating the instrument accordingly.

Kits

Also provided by the subject invention are kits for use in practicing the subject methods. The kits of the subject invention at least include a signal producing system as described above, where the signal producing system components may be combined into a single reagent composition or separated, e.g., present in separate containers. In certain embodiments, the signal producing system will be present in the kits in the form of a reagent test strip, as described supra. The subject kits may further include a means for obtaining a physiological sample. For example, where the physiological sample is blood, the subject kits may further include a means for obtaining a blood sample, such as a lance for sticking a finger, a lance actuation means, and the like. In addition, the subject kits may include a control solution or standard, e.g. an analyte control solution that contains a standardized concentration of analyte. In certain embodiments, the kits also include an automated instrument, as described above, for detecting the amount of product produced on the strip following sample application and relating the detected product to the amount of analyte in the sample.

In addition to above mentioned components, the subject kits typically further include instructions for using the components of the kit to practice the subject methods with the subject devices. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

The following examples are offered by way of illustration and not by way of limitation.

EXPERIMENTAL

Example 1, In Aqueous Form 0.1 M MES, pH 6.5, WST-5 6.75 mM, NaNO2 (0 or 0.3M)

Figure 2:
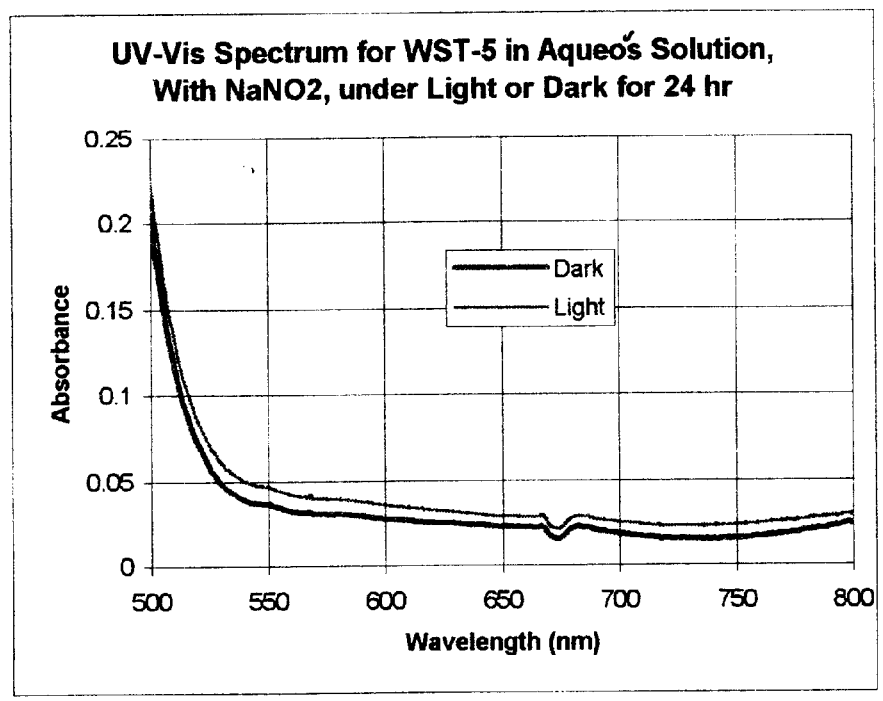
FIG. 2 provides the UV-Vis spectrum for WST-5 in aqueous solution, with $NaNO_2$, under light or dark for 24 hr.

The above solutions were set under light or dark for 24 hr individually. The solution was measured by UV-Vis by 10 fold dilution. The results are shown in FIGS. 1 & 2. FIG. 1 shows the result of the solution without $NaNO_2$, the solution was set in dark or under the light respectively. FIG. 2 shows the result of the solution with $NaNO_2$, the solution was set in dark or under the light respectively.

Example 2, In Dry Form

TABLE 1

Dry form Components Table

| Components | Quantity |
| --- | --- |
| Water | 100 ml |
| (N-[2-Hydroxyethyl]piperazine-N'-N[4-butanesulfonic acid, sodium salt (HEPES, FW 260.3, Sigma, St. Louis, MO, USA) | 1.3 gm |
| Borax decahydrate (FW 381.4, Sigma, St. Louis, MO, USA) | 3.0 gm |
| Gantrez* 6% | 20 mL |
| Pluronic L-64 (BASF Corporation, Moun Olive, New Jersey, USA) | 1.5 gm |
| Robose (MW 182, Sigma, St. Louis, MO, USA) | 5 gm |
| Sodium Nitrite (MW69, Aldirch Chemicals, Milwaukee, WI, USA | 0 or 2 gm |
| WST-5 (MW 1331.37, Dojindo) | 0.9 gm |
| Adjusut pH to 6.0 by adding NaOH | |
| Glucose Oxidase (GO, TOYOBO) | 100 KU |

*Gantrez AN-139 (Poly Methylvinylether-alt-Maleic Anhydride, MW 1,080,000, Cat# 41632-0, Aldrich Chemicals, Milwaukee, WI, USA) Make 6% Gantrez in water, heat to 95 C. for less than 45 min. to get Gantrez 6% which is ready to use.

Figure 3:
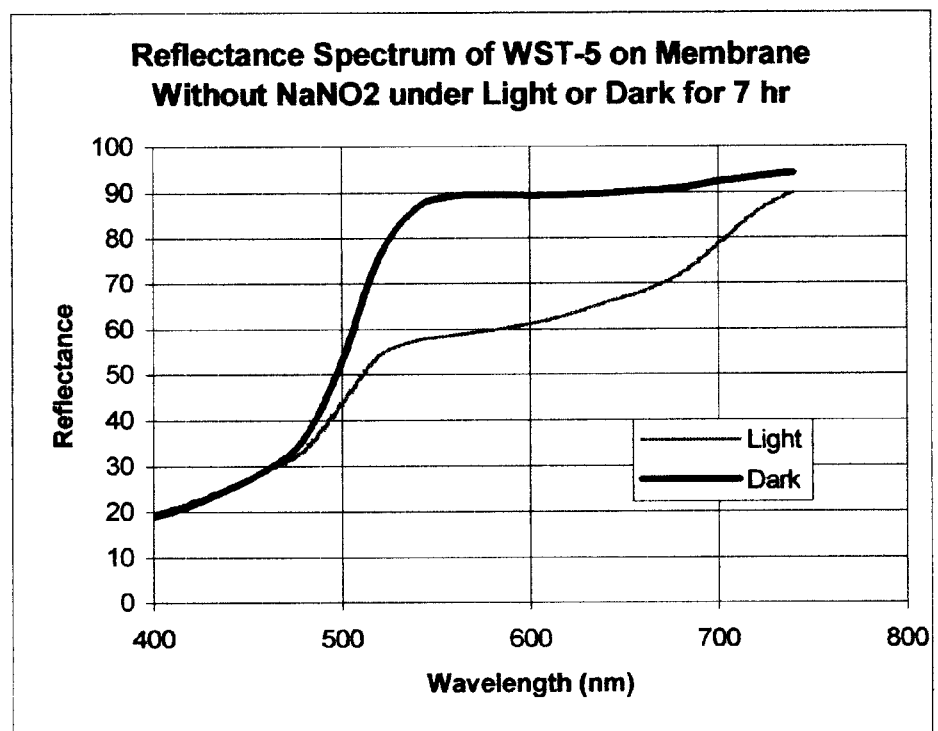
FIG. 3 provides the reflectance spectrum of WST-5 on a membrane without $NaNO_2$ under light or dark for 7 hr.
Figure 4:
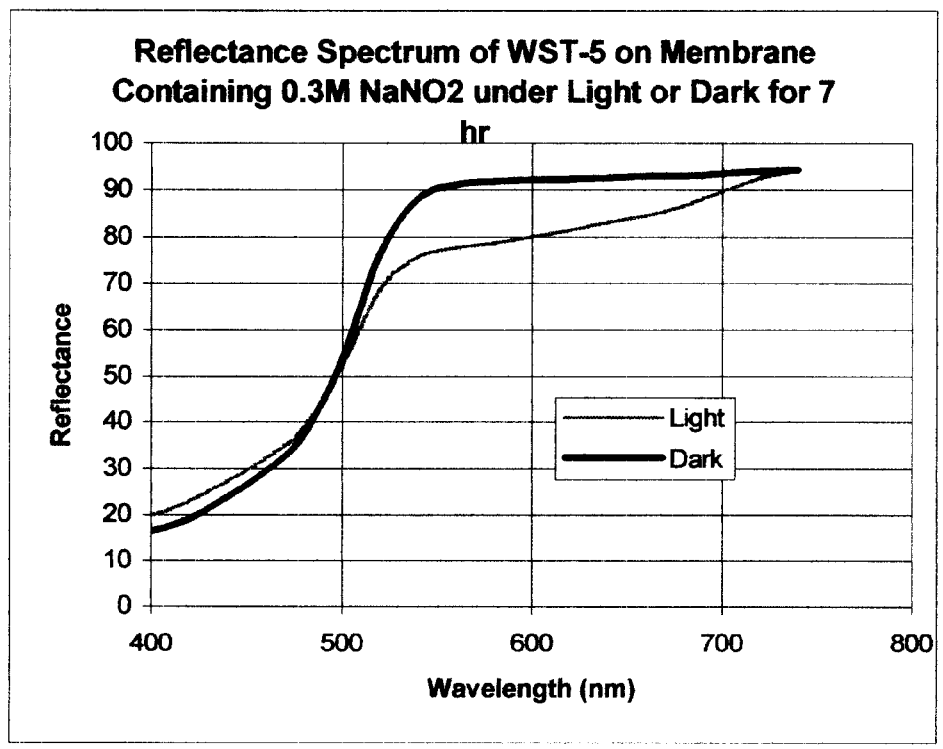
FIG. 4 provides the reflectance spectrum of WST-5 on a membrane containing 0.3 M $NaNO_2$ under light or dark for 7 hr.

A 0.8 μm nylon membrane obtained from Pall Corporation (East Hills, N.Y.) was dipped into the reagent of Table 1, until saturated. The excess reagent was scraped off gently with a glass rod. The resulting membrane was hung to dry in a 56° C. oven for 10 minutes The membrane was coated with and without sodium nitrite was set in set under light or dark for 7 hr individually. The reflectance of the membrane was measured by Macbath. The results are shown in FIGS. 3 & 4. FIG. 3 shows the result of the membrane without $NaNO_2$, the membrane was set in dark or under the light respectively. FIG. 4 shows the result of the membrane with $NaNO_2$, the membrane was set in dark or under the light respectively.

It is evident from the above results and discussion that the subject invention provides for improvement over previous tetrazolium dye reagent compositions, in that it provides for a convenient way to stabilize the dye component so that light exposure does not adversely effect the dye. As such, the subject invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A reagent composition comprising:
   a tetrazolium dye; and
   an effective amount of a nitrite stabilizing agent.

2. The composition according to claim 1, wherein said tetrazolium dye is a water soluble tetrazolium salt.

3. The composition according to claim 1, wherein said nitrite stabilizing agent is a nitrite salt.

4. The composition according to claim 1, wherein said reagent composition comprises an analyte oxidizing signal producing system.

5. The composition according to claim 4, wherein said analyte oxidizing signal producing system comprises an analyte oxidase.

6. The composition according to claim 4, wherein said analyte oxidizing signal producing system comprises an analyte dehydrogenase.

7. The composition according to claim 4, wherein said analyte oxidizing signal producing system further comprises an electron transfer agent.

8. The composition according to claim 4, wherein said analyte oxidizing signal producing system further comprises an enzyme cofactor.

9. The composition according to claim 1, wherein said composition is a fluid composition.

10. The composition according to claim 1, wherein said composition is a dry composition.

11. A reagent test strip comprising:
    a substrate; and
    an analyte oxidizing signal producing system present on said substrate, wherein said analyte oxidizing signal producing system includes a water soluble tetrazolium salt and a nitrite stabilizing agent.

12. The test strip according to claim 11, wherein said water soluble tetrazolium salt accepts a hydride to produce a water soluble formazan product.

13. The test strip according to claim 11, wherein said nitrite stabilizing agent comprises a nitrite salt.

14. The test strip according to claim 11, wherein said analyte oxidizing signal producing system comprises an analyte oxidase.

15. The test strip according to claim 14, wherein said analyte oxidizing signal producing system further comprises an electron transfer agent.

16. The test strip according to claim 14, wherein said analyte oxidizing signal producing system further comprises an enzyme cofactor.

17. The test strip according to claim 10, wherein said analyte oxidizing signal producing system is a glucose oxidizing signal producing system.

18. An analyte detection or measurement system comprising:
    (a) a reagent test strip comprising:
        (i) a substrate; and
        (ii) an analyte oxidizing signal producing system present on said substrate, wherein said signal producing system includes a water soluble tetrazolium salt capable of accepting a hydride to produce a water soluble formazan and a nitrite stabilizing agent; and
    (b) an automated instrument.

19. A method for detecting the presence or determining the concentration of an analyte in a sample, said method comprising:
    (a) applying said physiological sample to a reagent test strip comprising:
        (i) a substrate; and
        (ii) an analyte oxidizing signal producing system present on said substrate, wherein said signal producing system includes a water soluble tetrazolium salt capable of producing a water soluble formazan product and a nitrite stabilizing agent to produce a spot comprising said formazan product on said substrate;
    (b) detecting said spot; and
    (c) relating said detected spot to the presence or concentration of said analyte in said physiological sample.

20. The method according to claim 19, wherein said signal producing system further comprises an analyte oxidase.

21. The method according to claim 20, wherein said signal producing system further comprises at least one of an electron transfer agent.

22. The method according to claim 19, wherein said sample is whole blood or a derivative thereof.

23. The method according to claim 19, wherein said detecting and relating steps are carried out by an automated instrument.

24. A kit for use in determining the concentration of an analyte in a physiological sample, said kit comprising:
    (a) a reagent test strip comprising:
        (i) a substrate; and
        (ii) an analyte oxidizing signal producing system present on said substrate, wherein said signal producing system includes a water soluble tetrazolium salt capable of producing a water soluble formazan product and a nitrite stabilizing agent; and
    (b) at least one of:
        (i) a means for obtaining said physiological sample and
        (ii) an analyte standard.

25. The kit according to claim 24, wherein said means for obtaining said physiological sample is a lance.

26. The kit according to claim 24, wherein said analyte standard comprises a standardized concentration of a known reagent.

27. The kit according to claim 24, wherein said kit comprises a means for obtaining said physiological sample and an analyte standard.

28. A method for stabilizing a tetrazolium dye in a reagent composition, said method comprising:
    including in said reagent composition an effective amount of a nitrite stabilizing agent.

29. The method according to claim 28, wherein said nitrite stabilizing agent is a nitrite salt.

30. The method according to claim 29, wherein said nitrite salt is sodium nitrite.

31. The method according to claim 28, wherein said reagent composition is a dry composition.

32. The method according to claim 28, wherein said reagent composition is a wet composition.

* * * * *